United States Patent

Thiele et al.

[11] Patent Number: 5,945,367
[45] Date of Patent: Aug. 31, 1999

[54] METALLOCENES WITH SILYL-SUBSTITUTED BRIDGES AND THEIR USE FOR OLEFIN POLYMERIZATION

[75] Inventors: Karl Heinz Thiele, Halle; Christine Schliessburg, Merseburg, both of Germany; Eberhard Ernst, Katsdorf, Austria; Jens Reussner, Traun, Austria; Benno Bildstein, Innsbruck, Austria; Peter Denifl, Gries am Brenner, Austria

[73] Assignee: Borealis AG, Austria

[21] Appl. No.: 08/981,257

[22] PCT Filed: Jun. 28, 1996

[86] PCT No.: PCT/EP96/02828

§ 371 Date: Dec. 22, 1997

§ 102(e) Date: Dec. 22, 1997

[87] PCT Pub. No.: WO97/02276

PCT Pub. Date: Jan. 23, 1997

[30] Foreign Application Priority Data

Jul. 3, 1995 [AU] Australia ............................. 1126/95

[51] Int. Cl.$^6$ ....................................... C08F 4/64
[52] U.S. Cl. ................. 502/155; 502/152; 526/127; 526/160; 526/351; 526/352; 526/943; 526/12; 526/43; 526/53
[58] Field of Search ................. 502/152, 155; 526/127, 160, 943, 351, 352; 556/12, 43, 53

[56] References Cited

U.S. PATENT DOCUMENTS 5,541,350   7/1996   Murata et al. ............................. 556/10
5,767,209   6/1998   McNally .................................... 526/160

*Primary Examiner*—David W. Wu
*Attorney, Agent, or Firm*—Wenderoth, Lind & Ponack, L.L.P.

[57] ABSTRACT

The invention pertains to metallocenes of formula (I), wherein M is a metal group of the group of Ti, Zr, Hf, V, Nb and Ta or an element from the group of lanthanides; $X_1$ and $X_2$ stand for an alkyl, alkoxy, aryl, aryloxy, alkenyl, arylalkyl, alkylaryl or arylalkenyl group, hydrogen or halogen; $L_1$ and $L_2$ stand for a hydrocarbon which can form a sandwich structure with M; R stands for C, Si, Ge or Sn; and A and B stand for a trimethylsilyl radical, B optionally for an alkyl or aryl radical.

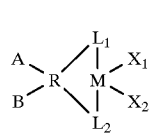

(I)

8 Claims, No Drawings

METALLOCENES WITH SILYL-SUBSTITUTED BRIDGES AND THEIR USE FOR OLEFIN POLYMERIZATION

BACKGROUND OF THE INVENTION

1. Field of Invention

The invention relates to new metallocenes and their use as catalysts in olefin polymerization.

2. Prior Art

Metallocenes of the metals of transition group IV of the Periodic Table of the Elements are highly active catalysts for the polymerization of olefins. The resulting polyolefins have new property combinations and supplement the product range of the polyolefins prepared hitherto using known conventional Ziegler-Natta catalysts.

It is known that catalysts based on unbridged, substituted and unsubstituted biscyclopentadienyl metallocenes in combination with aluminoxanes as cocatalyst can be used for the preparation of polyethylene and ethyleneolefin copolymers (EXXON EPA 128 046).

It is also known that stereoregular polyolefins can be prepared using bridged, chiral metallocenes. For bridging the ligand systems, use is mostly made of dimethylsilanediyl groups (CHISSO EPA 316 155), methylphenylsilanediyl groups (HOECHST EPA 320 762), ethylene groups (Brintzinger et al., J. Organomet. Chem., 288 (1985) 63–67) and isopropylidene bridges (Mitsui Toatsu EPA 459 264). Depending on the ligand type and the substituents, isotactic, syndiotactic, hemiisotactic, stereoblock-type and atactic homopolymers and copolymers having aliphatic or cyclic structures can be prepared.

As ligands, preference is given to using substituted and unsubstituted cyclopentadienyl units (CHISSO EPA 316 155), substituted and unsubstituted indenyl units (Hoechst EPA 302 424; Hoechst EPA 485 823) and also substituted and unsubstituted cyclopentadienyl units in combination with unsubstituted fluorenyl groups (Mitsui Toatsu EPA 412 416).

Likewise, it is known that bridged metallocenes having a cyclopentadienyl system and a heteroatom ligand (constrained geometry catalyst) can also be used for the polymerization of olefins (EXXON U.S. Pat. No. 5,096,867).

Among these various types of metallocene, the bridged, chiral, substituted bisindenyl systems have attained particular importance. Thus, it was able to be shown that the type of substituents and the position of the substituents on the ligand of the metallocene have a significant influence on the reactivity of the catalyst system and the stereoregular structure of the polyolefins obtained. Two possible substitution patterns in particular have been found to be advantageous. The first possibility entails substitution of the indenyl ligand in the 2, 4 and/or 6 position (Hoechst EPA 485823; Angew. Chem., 10 (1992) 1373) while the second possibility is fusion onto the benzene ring of the indenyl ligand (Organometallics 1994, 13, 964–970). Both types of catalyst can be used for preparing isotactic polypropylene and ethylene-α-olefin copolymers.

Multiply substituted indenyl ligands can be prepared only at considerable expense. Relatively simple systems having good activity and containing indenyl, 2-methylindenyl or 2-methylbenz[e]indenyl ligands give products, in particular polypropylene, having relatively low molar masses which are too low for many applications and represent the lower limit for industrial use.

It is therefore an object of the invention to find further structural variants of bridged metallocenes as catalysts for the polymerization of olefins which give polyolefins, in particular polypropylene, having relatively high molar masses.

BRIEF SUMMARY OF THE INVENTION

It has now surprisingly been found that silyl-substituted, diyl-bridged metallocene systems are suitable catalysts for the preparation of polyolefins and in particular of polypropylenes having relatively high molar masses.

The present invention accordingly provides metallocenes of the formula I

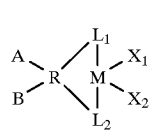

(I)

where M is a metal selected from the group consisting of Ti, Zr, Hf, V, Nb and Ta or an element selected from the group consisting of the lanthanides, $X_1$ and $X_2$ are identical or different and are each a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{20}$-arylalkyl group, a $C_7$–$C_{20}$-alkylaryl group, a $C_8$–$C_{20}$-aryl-alkenyl group, hydrogen or a halogen atom, $L_1$ and $L_2$
  a) are identical or different and are each an unsubstituted, monosubstituted or polysubstituted monocyclic or polycyclic hydrocarbon radical containing at least one cyclopentadienyl unit which can form a sandwich structure with M, or
  b) $L_1$ is an unsubstituted, monosubstituted or polysubstituted monocyclic or polycyclic hydrocarbon radical containing at least one cyclopentadienyl unit which can form a sandwich structure with M, and $L_2$ is an amido, phosphido or arsenido radical of the formula

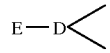

where D is nitrogen, phosphorus or arsenic and E is as defined for $X_1$ and $X_2$, R is carbon, silicon, germanium or tin, A and B are identical or different and are each a trimethylsilyl radical of the formula —Si(CH$_3$)$_3$, where B may also be a $C_1$–$C_{10}$-alkyl radical, preferably a $C_1$–$C_4$-alkyl radical, or a $C_6$–$C_{10}$-aryl radical.

DETAILED DESCRIPTION OF THE INVENTION

Preferred ligands $L_1$ and/or $L_2$ are substituted or unsubstituted cyclopentadienyl, indenyl or fluorenyl radicals. Particular preference is given to cyclopentadienyl, tetramethylcyclopentadienyl, indenyl, 2-methylindenyl, 2-methyl-4-phenylindenyl, 2-methyl-4,5-benzindenyl and fluorenyl units and also ferrocene- and ruthenocene-substituted units as are described, for example, in EP-A-673 946.

According to the invention, the following metallocenes are particularly preferred:
bis (trimethylsilyl)silanediyldicyclopentadienylzirconium dichloride,
bis(trimethylsilyl)silanediyldiindenylzirconium dichloride,
bis(trimethylsilyl)silanediylbis(2-methylindenyl)-zirconium dichloride,
bis(trimethylsilyl)silanediylbis(2-methyl-4,5-benz-indenyl) zirconium dichloride,
bis(trimethylsilyl)silanediylbis(2-methyl-4-phenyl-indenyl) zirconium dichloride,
bis(trimethylsilyl)silanediylbis(2-methyl-4-naphthyl-indenyl)zirconium dichloride,
bis(trimethylsilyl)silanediyldifluorenylzirconium dichloride,
bis(trimethylsilyl)silanediyl(fluorenyl)(cyclopenta-dienyl) zirconium dichloride,
bis(trimethylsilyl)silanediyl(fluorenyl)(indenyl)-zirconium dichloride and
bis(trimethylsilyl)silanediyl(tetramethylcyclopenta-dienyl)(indenyl)zirconium dichloride,
methyl(trimethylsilyl)silanediyldicyclopentadienyl-zirconium dichloride,
methyl(trimethylsilyl)silanediyldiindenylzirconium dichloride,
methyl(trimethylsilyl)silanediylbis(2-methylindenyl)-zirconium dichloride,
methyl(trimethylsilyl)silanediylbis(2-methyl-4,5-benz-indenyl)zirconium dichloride,
methyl(trimethylsilyl)silanediylbis(2-methyl-4-phenyl-indenyl)zirconium dichloride,
methyl(trimethylsilyl)silanediylbis(2-methyl-4-naphthyl-indenyl)zirconium dichloride,
methyl(trimethylsilyl)silanediyldifluorenylzirconium dichloride,
methyl-(trimethylsilyl)silanediyl(fluorenyl) (cyclopentadienyl)-zirconium dichloride,
methyl(trimethylsilyl)silanediyl(fluorenyl)(indenyl)-zirconium dichloride and
methyl(trimethylsilyl)silanediyl(tetramethylcyclopenta-dienyl)(indenyl)zirconium dichloride.

The invention further provides a process for preparing the metallocenes I, which comprises reacting a compound of the formula II

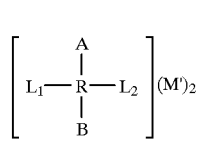
(II)

where $L_1$, $L_2$, A, B and R are as defined for formula I and M' is an alkali metal, preferably lithium, with a compound of the formula III $M(X')_2X_1X_2$ (III), where M, $X_1$ and $X_2$ are as defined for formula I and X' is a halogen atom, preferably chlorine.

The metallocenes I can be prepared, for example, according to the following reaction scheme:

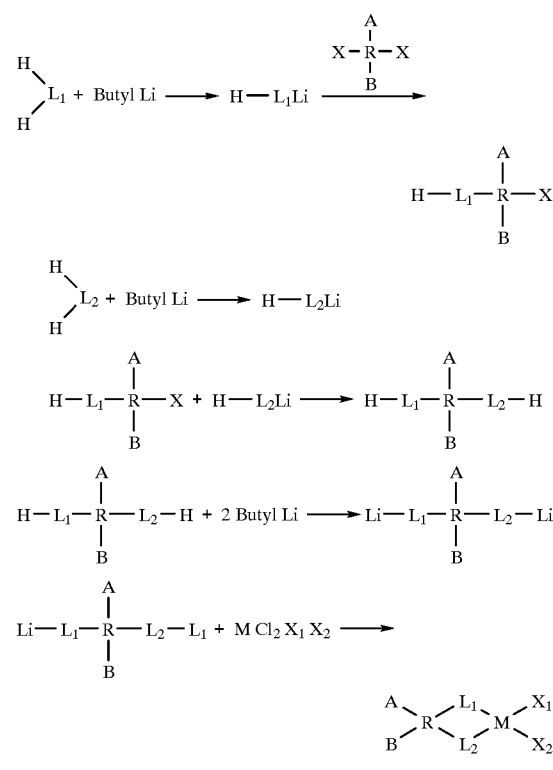

X = F; Cl; Br; J

X = F; Cl; Br; I $X_1$, $X_2$, $L_1$ and $L_2$ are as defined above.

In addition, amido, phosphido and arsenido radicals can be used as ligands $L_2$, where the substituents of these ligands are as defined for $X_1$ and $X_2$ or else are ferrocenyl- or ruthenocenyl-substituted or -fused. The reaction of the dimetallated compound of the formula II with the metal halide of the formula III in the last stage of the process of the invention can be carried out, for example, as described in EPA 659756. However, the reaction of the dimetallated compound of the formula II with the metal halide of the formula III in the last stage of the process of the invention is advantageously carried out in solvent mixtures of aromatic and/or aliphatic hydrocarbons, which may also be halogenated, with dialkyl ethers, preferably alkane/ether mixtures such as, for example, hexane/ether mixtures. The solvent mixtures preferably have transition energies $E_T(30)$ (empirical parameter as a measure of the polarity of solvents) in a range from 35.5 to 31.5 kcal/mol, particularly preferably from 34.5 to 32.5 kcal/mol. According to Chemical Reviews 1994, Vol. 94, No. 8, 2319 ff., the transition energy $E_T(30)$ is defined as the dependence of the band position and intensity of the chromophore pyridinium-N-phenoxide betaine on the solvent selected. When such charge-transfer complexes are dissolved, the longest wavelength absorption maximum undergoes a shift which increases with the polarity of the solvent. The transition energy $E_T(30)$ in kcal/mol is calculated from the measured frequency v of this maximum.

Suitable hydrocarbons and dialkyl ethers are, in particular, those which are listed, for example, in Chemical Reviews 1994, Vol. 94, No. 8, pp. 2337–2340. Examples of suitable aromatic hydrocarbons are compounds such as toluene, benzene or p-xylene. Aliphatic hydrocarbons can be, for example, all $C_5$–$C_{12}$-alkanes. Preference is given to n-pentane, n-hexane, n-heptane or cyclohexane. n-Hexane is of particular utility. Among the dialkyl ethers, preference is given to all di-$C_2$–$C_4$-alkyl ethers, for example diethyl ether, di-n-propyl ether, diisopropyl ether, di-n-butyl ether or tert-butyl-methyl ether. Examples of suitable halogenated hydrocarbons are all $C_1$–$C_4$-chloroalkanes. Particular preference is given to dichloromethane.

The invention further provides for the use of the metallocenes of the invention as polymerization catalysts in the polymerization of olefins, and also provides an olefin polymerization process in which the metallocenes of the invention are used as catalysts.

In the olefin polymerization, preference is given to using a cocatalyst, for example an aluminoxane of the formula IV for the linear type:

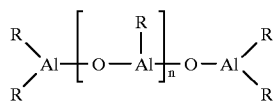

(IV)

and/or the formula V:

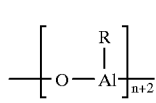

(V)

for the cyclic type, where, in the formulae IV and V, the radicals can be identical or different and are each a $C_1$–$C_6$-alkyl group and n is an integer of 1–50. Preferably, the radicals are identical and are methyl, isobutyl, phenyl or benzyl; particular preference is given to methyl. The aluminoxane can be prepared in various ways by known methods. One possibility is, for example, reacting aluminum alkyls with aluminum sulfate containing water of crystallization (Hoechst EP 302424). In the present invention, commercial MAO (methylaluminoxane, from Witco, Germany) is used.

It is also possible to mix the metallocene of the formula I with an aluminoxane of the formula IV and/or V before use in the polymerization reaction. The mixing is preferably carried out in solution Preference is given to dissolving the metallocene in an inert hydrocarbon and subsequently mixing it with the aluminoxane solution. Suitable inert hydrocarbons are aliphatic or aromatic hydrocarbons. Preference is given to using toluene. The concentration of the aluminoxane in the solution is in the range of 5–30% by mass, based on the total solution. The metallocene is preferably used in an amount of $10^{-4}$–1 mol per mol of aluminoxane. The mixing time is from about 5 minutes to 24 hours, preferably from 5 to 60 minutes. Mixing is usually carried out at a temperature of from −10 to +70° C., in particular from 10 to 40° C.

The metallocene can also be applied to a support. Suitable supports are, for example, the inorganic oxides of the metals of main groups II–IV of the Periodic Table. Preference is given to the oxides of the metals magnesium, calcium, aluminum, silicon, boron and their mixtures, for example the commercially available aluminum oxides "Alumina Typ C" (Degussa) and silicon oxides of the type "Silica Davison Grade 952–957" or of the "Aerosil" type (Degussa) and also mixtures of $Al_2O_3$ and $SiO_2$. Particular preference is given to catalyst supports as described in EP-A 685 494.

The polymerization can be carried out in solution, suspension or gas-phase processes, continuously or batchwise at a temperature of from −10 to +200° C., preferably from +20 to +80° C. Olefins of the formula $R^a$—CH═CH—$R^b$ are polymerized or copolymerized. In this formula, $R^a$ and $R^b$ are identical or different and are each a hydrogen atom or an alkyl radical having from 1 to 20 carbon atoms. However, $R^a$ and $R^b$ together with the carbon atoms connecting them can also form a ring. For example, olefins such as ethylene, propylene, 1-butene, 1-hexene, 4-methyl-1-pentene, 1-octene, cyclopentene, norbornene or norbornadiene are polymerized or copolymerized. In particular, ethylene, propylene and 1-butene are polymerized or copolymerized.

If necessary, hydrogen is added as molar mass regulator. The total pressure in the polymerization is 0.5–150 bar. Preference is given to carrying out the polymerization in a pressure range of 1–40 bar.

It has been found to be advantageous to carry out the reaction of the monomers in the presence of the metallocene catalyst system at a molar ratio of aluminum from the oligomeric aluminoxane compound to the transition metal of the metallocene compound of from $10^6$:1 to $10^1$:1, preferably from $10^4$:1 to $10^2$:1.

If the polymerization is carried out as a suspension or solution polymerization, use is made of an inert solvent. It is possible to use, for example, aliphatic or cycloaliphatic hydrocarbons such as pentane, hexane or cyclohexane. Toluene can also be used. Preference is given to carrying out the polymerization in the liquid monomer.

According to the invention, the copolymerization of ethylene with propylene is carried out in liquid propylene or in hexane as suspension medium. In the polymerization in liquid propylene, the ethylene is preferably introduced in such an amount that a partial pressure ratio $p_{c2}/p_{c3}$ of greater than 0.5, in particular greater than 1.0, is established above the liquid phase ($p_{c2}$=partial pressure of ethylene in the gas phase above the suspension; $p_3$=partial pressure of propylene in the gas phase above the suspension). In the copolymerization in hexane as suspension medium, an ethylene/propylene gas mixture having a propylene content of from 1 to 50 mol %, preferably from 5 to 30 mol %, is fed in. The total pressure is kept constant during the polymerization by metering in further amounts. The total pressure is from 0.5 to 40 bar, preferably from 1 to 20 bar.

The polymerization time is generally from about 10 minutes to 6 hours, preferably from 30 minutes to 2 hours.

The catalysts used according to the invention expand the range of polymerization-active metallocenes for preparing polyolefin homopolymers and copolymers. In particular, the metallocenes of the invention produce polymers and copolymers having a high, industrially relevant molar mass and a narrow molar mass distribution in the industrially important temperature range from 20 to 80° C.

A further advantage arises from the preferred metallocene preparation process of the invention which enables high yields of the pure racemate or pseudoracemate form of the resulting metallocene compound to be obtained stereoselectively in the reaction of the dimetallated ligand pairs of the formula II with the metal halide of the formula III using the preferred solvent mixtures, in particular ether/alkane mixtures. For the purposes of the present invention, pseudoracemates are compounds which have the same three-dimensional arrangement of the ligands as racemates, but are asymmetric because of the way in which the bridge is substituted.

The following examples illustrate the invention.

In the examples:

$M_W$=weight average molar mass in g/mol,
$M_n$=number average molar mass in g/mol,
$M_W/M_n$=molar mass distribution, determined by gel permeation chromatography,
MS=mass spectrometry $^1$H-NMR = $^1$H nuclear magnetic resonance spectroscopy } Elucidation of the catalyst structure
$^{13}$C-NMR = $^{13}$C nuclear magnetic resonance spectroscopy

EXAMPLE 1

Bis(trimethylsilyl) silanediyldicyclopentadienylzirconium dichloride

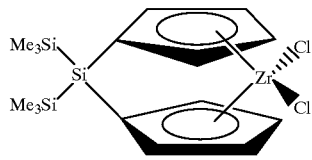

5 g (16.4 mmol) of bis(trimethylsilyl)dicyclopentadienylsilane (K. Hassler, K. Schenzel, *J. Organomet. Chem.* 484, $C_1$–$C_4$ (1994)) are dissolved in 20 ml of diethyl ether. The solution is cooled to −78° C. and admixed with 21 ml of a 1.55 molar solution of n-butyllithium in n-pentane. The solution is warmed to room temperature, the bis(trimethylsilyl)silanediyldicyclopentadienyldilithium is filtered off and dried under reduced pressure. The yield is 3.7 g (71.4% of theory).

1.1 g (3.5 mmol) of bis(trimethylsilyl)silanediyldicyclopentadienyldilithium are suspended in 50 ml of toluene. The suspension is cooled to −40° C. and admixed with 1.3 g (3.5 mmol) of zirconium tetrachloride bis(tetrahydrofuran). After warming to room temperature, the solution is stirred for 24 hours at room temperature and then filtered. The solvent is removed under reduced pressure, the residue is extracted with n-pentane and the extract is evaporated to dryness, leaving bis(trimethylsilyl) silanediyldicyclopentadienylzirconium dichloride. The yield is 600 mg (37.2% of theory).

MS (El, 70 eV, 200° C.): m/e=464 (100%), molecular peak; 354 (95%), 1-methylsilyl-3-silyl-2-silanediyl-2-dicyclo-pentadienylzirconium chloride radical cation; 318 (49%), 1-methylsilyl-3-silyl-2-silanediyl-2-dicyclopentadienyl-zirconium radical cation.

$^1$H-NMR ($C_6D_6$): 0.14 ppm (18 H, d); 5.87 ppm (4 H, t); 6.75 ppm (4 H, t); $^{13}$C-NMR (THF-$d_8$) 0.19 ppm; 103.97 ppm; 118.30 ppm; 125.90 ppm; 128.35 ppm

EXAMPLE II

Bis(trimethylsilyl)silanediyldiindenylzirconium dichloride (diastereomer mixture)

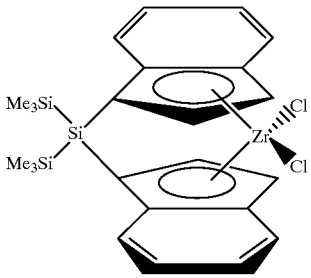

5 g (20.4 mmol) of 2,2-dichlorohexamethyltrisilane (G. Kolliger, *Thesis* 1993, Technical University of Graz) are initially charged in 50 ml of n-pentane. The solution is cooled to −78° C. and admixed with 5 g (40.8 mmol) of indenyllithium. After warming to room temperature, the solution is stirred for 24 hours, subsequently filtered, again cooled to −78° C. and 21 ml of a 1.58 molar solution of n-butyllithium in n-pentane are added dropwise. After warming to room temperature, the reaction mixture is filtered and the bis(trimethylsilyl)silanediyldiindenyldilithium obtained as filter cake is dried under reduced pressure. The yield is 3.5 g (40.9% of theory).

A solution of 3.5 g (8.4 mmol) of bis(trimethylsilyl)-silanediyldiindenyldilithium in 50 ml of toluene is cooled to −30° C. 3.1 g (8.3 mmol) of zirconium tetrachloride bis(tetrahydrofuran) are added to the suspension. After warming to room temperature, the reaction mixture is heated at 50° C. for 5 hours on a water bath and subsequently filtered. The solvent is removed under reduced pressure, the residue is taken up in n-pentane and the solution is filtered. Removal of the solvent under reduced pressure leaves the bis(trimethylsilyl)silanediyldiindenylzirconium dichloride. The yield is 1.2 g (25.5% of theory).

MS (El, 70 eV, 200° C.): m/e=564 (100%), molecular peak; 453 (29%), 1-trimethylsilyl-2-silanediyl-2-diindenylzirconium chloride radical cation; 389 (36%), 1-methylsilyl-2-silanediyl-2-diindenylzirconium radical cation; 289 (58%), 1-methylsilyl-2-silanediyl-2-diindenyl radical cation; $^1$H-NMR (THF-$d_8$): −0.0917 ppm (18 H, t); 5.65 ppm (2 H, d); 6.73 ppm (2 H, d); 7.13 ppm (8 H, m).

EXAMPLE III

Bis(trimethylsilyl)silanediylbis(2-methylindenyl)-zirconium dichloride

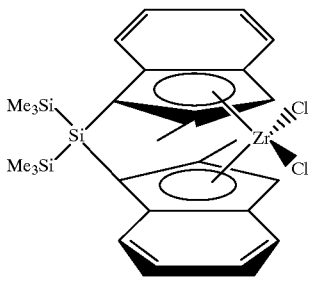

A solution of 3 g (20 mmol) of 2-methylindene (C. F. Koelsch, P. R. Johnsen, *J. Am. Chem. Soc.* 65, 567, (1943)) in 50 ml of diethyl ether is cooled to −78° C. and admixed with 14.6 ml of a 1.58 molar solution of n-butyllithium in n-pentane. The solution is warmed to room temperature and the 2-methylindenyllithium formed is filtered off and dried under reduced pressure. The yield is 2.5 g (91.9% of theory).

A solution of 2.5 g (18.4 mmol) of 2-methylindenyllithium in 50 ml of diethyl ether is added at −78° C. to 2.2 g (9.2 mmol) of 2,2-dichlorohexamethyltrisilane in 50 ml of n-pentane. After warming to room temperature, the reaction mixture is heated at 50° C. for 4 hours on a water bath, subsequently filtered warm, again cooled to −78° C. and admixed with 11.6 ml of a 1.58 molar solution of n-butyllithium in n-pentane. After warming to room temperature, the solution is filtered and the bis(trimethylsilyl)silanediylbis(2-methylindenyl)dilithium obtained as filter cake is dried under reduced pressure. The yield is 2.6 g (63.4% of theory).

1.8 g (4.9 mmol) of zirconium tetrachloride bis(tetrahydrofuran) are added at −30° C. to 2.2 g (4.9 mmol) of bis(trimethylsilyl)silanediylbis(2-methylindenyl)-dilithium in 50 ml of toluene. After warming to room temperature, the reaction mixture is heated at 50° C. for 4 hours on a water bath, subsequently filtered and the toluene is removed under reduced pressure. The residue is washed with n-pentane. After decanting off the n-pentane, the bis(trimethylsilyl)silanediylbis(2-methylindenyl)-zirconium dichloride is dried under reduced pressure. The yield is 800 mg (27.6% of theory).

MS (EI, 70 eV, 200° C.): m/e=596 (0.5%), molecular peak; 483 (4.7%), 1-trimethylsilyl-3-silyl-2-silanediyl-2-bis-(2-methylindenyl)zirconium radical cation; 441 (10.6%), 1-methylsilyl-3-silyl-2-silanediyl-2-bis(2-methylindenyl)zirconium radical cation; 383 (62.4%), 1-trimethylsilyl-3-silyl-2-silanediyl-2-bis(2-methylindenyl) radical cation; 348 (26%), 1-dimethylsilyl-2-bis(2-methylindenyl)silyl radical cation; 129 (100%), bis(2-methylindenyl) radical cation; 115 (61.3%), 2-methylindenyl radical cation.

$^1$H-NMR (THF-$d_8$): −0.0621 ppm (18 H, t); 2.26 ppm (6 H, s); 5.878 ppm (2 H, s); 6.4069 ppm (2 H. d); 7.1–7.2 ppm (8 H, m)

EXAMPLE IV

Methyl(trimethylsilyl)silanediylbis(2-methylindenyl)-zirconium dichloride

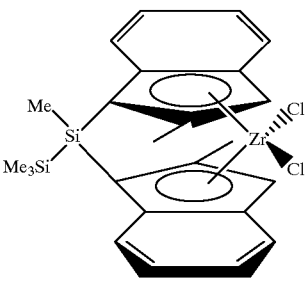

25.6 ml of a 1 molar methyllithium solution (25.6 mmol) are added under argon at −80° C. to a solution of 4.35 g (11.6 mmol) of 1,1,2-tetramethylbis(2-methylindenyl)-disilane [M.Kumada, T. Kondo, K. Mimura, M. Ishikawa, K. Yamamoto, S. Ikeda, M. Kondo; *J. Organomet. Chem.* 43 (1972) 293] in 50 ml of absolute diethyl ether. The reaction mixture is brought to room temperature over a period of 5 hours and stirred further for 13 hours at room temperature. After taking off the solvent in a high vacuum, a white residue is obtained. This is admixed with 100 ml of absolute n-hexane, the resulting suspension is filtered under argon and the filtration residue is washed 5 times with absolute n-hexane. After drying for 2 hours in a high vacuum, 4.43 g of the corresponding dilithium salt (98.7% yield) is obtained as a white, pyrophoric powder which is used without further purification for the synthesis of the zirconocene dichloride.

A suspension of 2.68 g of zirconium tetrachloride (11.5 mmol) in 50 ml of absolute n-hexane is added at −85° C. to a solution of 4.43 g of the dilithium salt (11.5 mmol) in 50 ml of absolute diethyl ether. After warming to room temperature, the mixture is stirred for 52 hours at room temperature. After taking off the solvent in a high vacuum, the solid residue is washed once with absolute n-hexane and twice with a little absolute diethyl ether, taken up in 50 ml of absolute methylene dichloride, filtered under argon and the filtrate is evaporated in a high vacuum until precipitate formation commences. After 2 days at −20° C., the precipitate formed is filtered off, washed a number of times with a little absolute n-hexane and dried in a high vacuum. This gives 5.18 g of methyl(trimethylsilyl)-silanediylbis(2-methylindenyl)zirconium dichloride (84.4% yield; rac: meso=20) as a yellow, microcrystalline powder.

$C_{24}H_{28}Si_2ZrCl_2$ (534.79 g/mol); MS (EI. 30 eV) [m/e (%)]: M$^+$: 534 (100), M$^+$—Me: 519 (8), M$^+$—Cl: 499 (8), M$^+$—Cl—Me: 484 (12), M$^+$—SiMe$_3$: 461 (100), M$^+$SiMe$_3$—Cl-2H: 424 (31), M$^+$SiMe$_3$—Cl—Me—2H: 409 (18); $^1$H-NMR (CD$_2$C$_2$) [ppm]: 0.57 (9H, s, Si(CH$_3$)$_3$); 1.44 (3H, s, Si(CH$_3$)); 2.20 and 2.27 (6H, each s, (CH$_3$)-Ind); 6.65 to 7.82 (10H, m, Ind).

POLYMERIZATION EXAMPLES

Example 1

After being made inert, a 2 l stirred reactor is charged at room temperature with 6.6 g of 10% strength MAO and 300 g of liquid, purified propylene and the mixture is stirred for 15 minutes.

5 mg of bis(trimethylsilyl)silanediyldicyclopentadienylzirconium dichloride are dissolved in 2.4 ml of toluene and mixed with 6.6 g of 10% strength MAO. The catalyst solution is subsequently injected into the reactor with a further 200 g of propylene and the mixture is heated to the polymerization temperature of 70° C. which is kept constant for a period of 2 hours. The reaction is stopped after 1 hour by flashing off the propylene. This gave 106.3 g of polypropylene having a molar mass $M_w$=25,000 g/mol and a polydispersity $M_w/M_n$=2.9.

Example 2

After being made inert, a 2 l stirred reactor is charged under nitrogen with 3.9 g of 10% strength MAO and 1 dm$^3$ of n-hexane and the mixture is stirred for 15 minutes. After degassing the suspension medium and heating the reactor to the reaction temperature of 70° C., the polymerization is started by injecting the catalyst solution together with an ethylene/propylene mixture containing 11.3 molt of propylene.

The catalyst solution is prepared by dissolving 3 mg of bis(trimethylsilyl)silanediyldicyclopentadienylzirconium dichloride in 1.4 ml of toluene and mixing with 4.0 g of 10% strength MAO.

The pressure in the reactor is kept constant at 2 bar during the entire polymerization time by metering in further amounts of the gas mixture. The stirrer speed is 700 revolutions per minute and the polymerization time is 2 hours.

This gave 14.8 g of ethylene-propylene copolymer having a molar mass $M_w$=134,000 g/mol and a polydispersity $M_w/M_n$=6.3. The propylene content is 2.7 mol %.

Example 3

The experiment is carried out using a method similar to Example 1. No MAO is included in the initial charge in the reactor. The catalyst solution is prepared by dissolving 5 mg of bis(trimethylsilyl)silanediyldiindenyl-zirconium dichloride in 3.6 ml of toluene and mixing with 9.2 g of 30% strength MAO.

This gave 45.7 g of polypropylene having a molar mass $M_w$=42,000 g/mol and a polydispersity $M_w/M_n$=2.0.

Example 4

After being made inert, a 2 l stirred reactor is charged under nitrogen with 1 dm$^3$ of purified n-hexane. After degassing the suspension medium and heating the reactor to the reaction temperature of 70° C., the polymerization is started by injecting the catalyst solution together with ethylene.

The catalyst solution is prepared by dissolving 2 mg of bis(trimethylsilyl)silanediyldiindenylzirconium dichloride in 1.7 ml of toluene and mixing with 3.7 g of 30k strength MAO.

The pressure in the reactor is kept constant at 2 bar during the entire polymerization time by metering in further amounts of the monomer. The stirrer speed is 700 revolutions per minute and the polymerization time is 1 hour.

This gave 25.4 g of polyethylene having a molar mass $M_w$=445,000 g/mol and a polydispersity $M_w/M_n$=5.8.

Example 5

The experiment is carried out using a method similar to Example 1. No MAO is included in the initial charge in the reactor. The catalyst solution is prepared by dissolving 6 mg of bis(trimethylsilyl)silanediylbis(2-methylindenyl)zirconium dichloride in 3.2 ml of toluene and mixing with 10.5 g of 30% strength MAO. The reaction time is 2 hours.

This gave 48.3 g of polypropylene having a molar mass $M_w$=336,000 g/mol and a polydispersity $M_w/M_n$=2.2.

Example 6

The experiment was carried out using a method similar to Example 1. No MAO is included in the initial charge in the reactor. The catalyst solution is prepared by dissolving 5 mg of bis(trimethylsilyl)silanediylbis(2-methylindenyl)zirconium dichloride in 26.2 g of 30% strength MAO. The reaction time is 2 hours.

This gave 92 g of polypropylene having a molar mass $M_w$=248,000 g/mol and a polydispersity $M_w/M_n$=2.0.

Example 7

After being made inert, a 2 l stirred reactor is charged at room temperature with 500 g of liquid, purified propylene and is subsequently heated to 70° C. 5 mg of bis(trimethylsilyl)silanediylbis(2-methylindenyl)-zirconium dichloride are dissolved in 2.8 ml of toluene and mixed with 8.7 g of 30% strength MAO. The catalyst solution is injected into the reactor together with ethylene. An ethylene partial pressure of 1 bar is maintained over the reaction time of 2 hours. The reaction is stopped by flashing off the monomers.

This gave 174.4 g of an ethylene/propylene copolymer having a molar mass $M_w$=101,000 g/mol and a polydispersity $M_w/M_n$=2.7. The propylene content is 16.6 mole %.

Example 8

The experiment is carried out using a method similar to Example 1. The reactor is initially charged with 0.76 g of 30% strength MAO. The catalyst solution is prepared by dissolving 6.4 mg of methyl(trimethylsilyl)silanediylbis-(2-methylindenyl)zirconium dichloride in 20 ml of toluene. 0.6 ml are mixed with 0.5 g of 30% strength MAO and introduced into the reactor. The reaction time is 2 hours.

This gave 62.9 g of polypropylene having a molar mass $M_w$=249,000 g/mol and a polydispersity $M_w/M_n$=2.6.

We claim:

1. A metallocene of the formula I

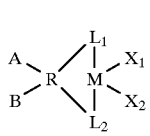

(I)

where M is a metal selected from the group consisting of Ti, Zr, Hf, V, Nb and Ta or an element selected from the group consisting of the lanthanides, $X_1$ and $X_2$ are identical or different and are each a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{20}$-arylalkyl group, a $C_7$–$C_{20}$-alkylaryl group, a $C_8$–$C_{20}$-arylalkenyl group, hydrogen or a halogen atom, $L_1$ and $L_2$
a) are identical or different and are each a monocyclic or polycyclic hydrocarbon radical containing at least one cyclopentadienyl unit which can form a sandwich structure with M, or
b) $L_1$ is a monocyclic or polycyclic hydrocarbon radical containing at least one cyclopentadienyl unit which can form a sandwich structure with M, and $L_2$ is an amido, phosphido or arsenido radical of the formula

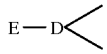

where D is nitrogen, phosphorus or arsenic and E is as defined for $X_1$ and $X_2$,
R is carbon, silicon, germanium or tin,
A is trimethylsilyl radical of the formula —Si(CH$_3$)$_3$ and B is a trimethysilyl radical of the formula —Si(CH$_3$)$_3$, a $C_1$–$C_{10}$-alkyl radical or a $C_6$–$C_{10}$-aryl radical.

2. A metallocene as claimed in claim 1, wherein the ligands $L_1$ and/or $L_2$ are substituted or unsubstituted cyclopentadienyl, indenyl or fluorenyl radicals.

3. The process for preparing a metallocene of the formula I as claimed in claim 1, which comprises reacting a compound of the formula II

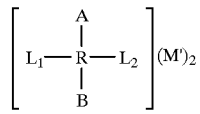 (II)

with a compound of the formula III $$M(X')_2 X_1 X_2 \qquad (III)$$

where $L_1$, $L_2$, A, B, R, M, $X_1$, $X_2$ are as defined in claim 1, M' is an alkali metal and X' is a halogen atom.

4. The process for preparing a metallocene of the formula I as claimed in claim 3, wherein the reaction of the compound II with the compound III is carried out in solvent mixtures of aromatic and/or aliphatic hydrocarbons, which may also be halogenated, with dialkyl ethers.

5. The process as claimed in claim 4, wherein the solvent mixtures have transition energies $E_T(30)$ in a range from 35.5 to 31.5 kcal/mol.

6. The process as claimed in claim 4, wherein a compound of the formula II as a solution in dialkyl ethers is reacted with a compound of the formula III as a suspension in aromatic and/or aliphatic hydrocarbons which may also be halogenated, where the solvent mixture has a transition energy $E_T(30)$ of from 35.5 to 31.5 kcal/mol.

7. A process for preparing polyolefins by polymerization of olefins, wherein a metallocene as claimed in claim 1 is used as catalyst.

8. The process for preparing polyolefins as claimed in claim 7, wherein an aluminoxane is used as cocatalyst in addition to the metallocenes.

* * * * *